United States Patent [19]
Knott et al.

[11] 3,983,118
[45] Sept. 28, 1976

[54] PRODUCTION OF N⁵-METHYLTETRAHYDROHOMOFOLIC ACID AND RELATED REDUCED DERIVATIVES OF HOMOFOLIC ACID

[75] Inventors: Roger L. Knott; Taunton-Rigby, both of Waltham, Mass.; John A. R. Mead, Bethesda, Md.

[73] Assignee: The United States of America as represented by the Department of Health, Education and Welfare, Washington, D.C.

[22] Filed: Aug. 16, 1974

[21] Appl. No.: 498,187

Related U.S. Application Data

[63] Continuation-in-part of Ser. No. 263,559, June 16, 1976, Pat. No. 3,870,719.

[52] U.S. Cl. .............................................. 260/251.5
[51] Int. Cl.² .......................................... C07D 475/04
[58] Field of Search ................................. 260/251.5

[56] References Cited
OTHER PUBLICATIONS

Gupta et al. – Archiv. Biochem and Biophys 120, 712–718 (1967).

*Primary Examiner*—Raymond V. Rush
*Attorney, Agent, or Firm*—John S. Roberts, Jr.; Norman J. Latker; Thomas G. Ferris

[57] ABSTRACT

The preparation of N⁵-methyltetrahydrohomofolic acid and alkali metal salts thereof is from homofolic acid starting material (HFA) by catalytic reduction with platinum oxide in the dark under hydrogen at a slight overpressure to produce tetrahydrohomofolate (THHF), them immediately reacting this product with formaldehyde to produce 5,11-methylenetetrahydrohomofolate and reducing this methylene intermediate without isolation with sodium borohydride to give the desired 5-methyltetrahydrohomofolate in the disodium salt form. The 5-methyl product is recovered by precipitating side products at a pH of about 3.8 with acetic acid and refrigerating the product filtrate overnight at about 3°–10°C. The filtrate containing the product 5-methyltetrahydrohomofolate (5-MeTHHF) is treated with charcoal, concentrated to an oil and the 5-methyl product is precipitated with absolute ethanol. The 5,11-methylenetetrahydrofolate may be separately recovered and in a second reaction an additional product known as the 5,11-methenyl is formed by reaction with formic acid. These products show increased stability over folate analogues and show biological promise in the treatment of cancer and leukemia as antifolates and specifically against L1210-FR8 tumor in mice.

1 Claim, No Drawings

PRODUCTION OF N⁵-METHYLTETRAHYDROHOMOFOLIC ACID AND RELATED REDUCED DERIVATIVES OF HOMOFOLIC ACID

This application is a continuation in part in Ser. No. 263,559, Knott et al, filed June 16, 1972, for "Synthesis of N$^5$-Methyltetrahydrohomofolic Acid and Related Reduced Derivatives of Homofolic Acid" now U.S. Pat. No. 3,870,719.

The present invention is directed towards the methods of preparation and recovery of certain folic acid antagonists which are related to 5,6,7,8 tetrahydrohomofolic acid which, due to its instability, is limited in utilization. The subject of folate antagonists has been recently studied in J. R. Bertino, Folate Antagonists as Chemotherapeutic Agents, *Annals of New York Academy of Science*, Vol. 186, 1971; and also treated in Goodman and Gilman, *Pharmacological Basis for Therapeutics*, 4th Edition, 1970, pages 1431–1444.

In the patent art the production of tetrahydrohomofolic acid salts is set out in:

U.S. Pat. No. 3,468,886 Mosher et al. (USA—HEW)
U.S. Pat. No. 3,637,695 Kim et al. (USA—HEW)

The folic acid molecule reproduced below is generally viewed as consisting of three segments. The first segment is a pteridine moiety which is a fused diazine with a pyrimidine A ring and a 1,4 diazine B ring. A methylene bridge at C$^9$ connects the first and second segments. The second segment is a paraaminobenzoic fraction, and the third is a glutamic acid residue.

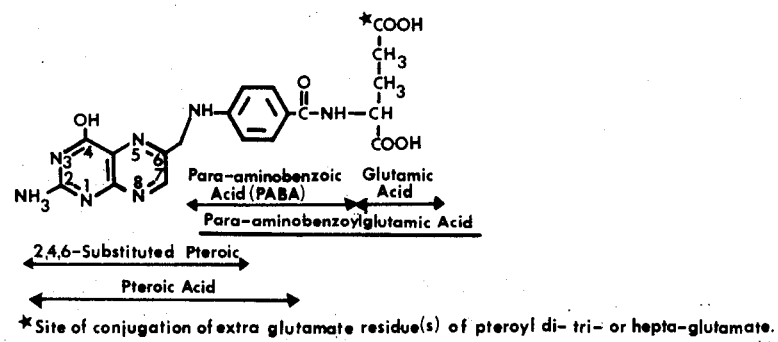

Folic Acid (Pteroylglutamic Acid)

Also reproduced is the structure of 5,6,7,8-tetrahydrofolic acid and compounds in the folic series analogous to the present compounds.

| | | |
|---|---|---|
| N$^{5,10}$methenyl THFA | >CH | formate |
| N$^{5,10}$methylene THFA | >CH$_2$ | formaldehyde |
| N$^5$methyl THFA | —CH$_3$ | methanol |

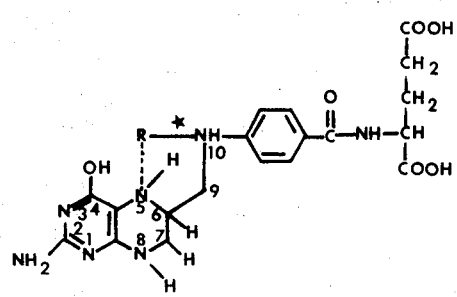

*Broken lines indicate the N$^3$ and/or N$^{10}$ site of attachment of various 1-carbon units for which THFA acts as a carrier.

5,6,7,8-Tetrahydrofolic Acid (THFAXFH$_4$XR=—H)

Homofolic acid differs from folic acid in being an analogue where an additional methylene or CH$_2$ group is inserted between C$^9$ and N$^{10}$ of the basic folic molecule. Tetrahydrofolic acid is a derivative of folic acid wherein the 5, 6, 7, and 8 positions are hydrogenated.

The most important folic acid derivatives which have been isolated from living systems are 5-methyl, 5,10-methenyl, and 5,10-methylenetetrahydrofolic acids. The homofolic acid derivatives analogous to these compounds are, therefore, the most likely candidates as synthesis for folic acid antagonists to compete with folic and affect its single carbon unit transfer function.

The production of 5-methyltetrahydrofolate in the literature dates at least from 1963 when W. Sakami in Biochem. Prep. 10, 103 (1963) produced 5,10-methylenetetrahydrofolate by reacting tetrahydrofolic acid with formaldehyde and subsequently reduced the methylenetetrahydrofolate with potassium borohydride. The crude 5-methyltetrahydrofolate (MeTHF) formed in this procedure was purified by gradient elution chromatography on DEAE cellulose. V. S. Gupta and F. M. Huennekens in Arch. Biochem. Biophys., 120, 712–718 (1967) followed a similar procedure with the tetrahydrofolate derivatives which also involve condensation of formaldehyde with tetrahydrofolate to yield 5,10-methylenetetrahydrofolate followed by reductive cleavage with the latter of borohydride. Gupta et al found that little or no cleavage occurred on the N$^5$ side of the methylene bridge and thus the production of the 5-methyl variety was practically exclusive.

The present invention differs from the art noted above in that homofolic acid is utilized as a starting material instead of folic acid and in the procedure following there are several important differences designed to obviate the difficulties encountered by the fragility of tetrahydrohomofolic acid (THHF).

In the present procedure homofolic acid (NSC 79249) is reduced catalytically in the dark using a platinum oxide catalyst. The catalyst is removed under an inert gas such as argon and the resulting tetrahydrohomofolate which is obtained in aqueous solution is immediately reacted with formaldehyde without light to produce the intermediate 5,11-methylenetetrahydrohomofolate. This intermediate, again without isolation, is reduced with an alkali metal borohydride such as sodium borohydride to give the desired product, 5-methyltetrahydrohomofolic acid in the disodium salt form. The procedure thus far emphasizes a rapid sequential process differing from the stepwise process of the prior art as well as utilizing a different starting material.

By use of acetic acid in place of hydrochloric acid and adjusting the pH to 3.8, inorganic salts such as sodium acetate and boric acid are cleanly separated with alcohol (i.e., ethanol) in which they are soluble but from which the desired product, 5-methyl THHF, precipitates essentially quantitatively. The preferred procedures call for an overnight refrigeration of the impure solution at 3°–10°C followed by filtration of impurities. The product in solution may be treated with charcoal, concentrated to an oil, and precipitated with ethanol (absolute). The yields obtained after trying are in the area of 68%.

With regard to the efficacy of acetic acid over mineral acids, such as HCl, HBr, HI, and $HNO_3$, it was found that the acetic acid which formed a sodium acetate salt in the process above could be leached out with ethanol, whereas the salts formed by hydrochloric, for example, could not. Additionally, the optimum pH of 3.8 noted above was arrived at after batch experiments showed that the solution clouded over at a pH of 4.0 and cleared again at a pH of 3.5 or above. The pH of 3.7–3.8 and optimally a pH of 3.8 was selected by experimentation as being optimum values for precipitation of the impurities which came down and were removed after overnight refrigeration at 3°–10°C. The precipitant was beige in color.

The reaction is carried out in the dark or without light as a safety precaution due to the fragility of the THHF intermediate in the process. The THHF has historically been known as an unstable intermediate and this protection for yield was deemed a necessary precaution.

This procedure of separating the sensitive 5-methyl THHF product eliminates the time-consuming DEAE column chromatography step and based on prior procedures with the folate increased the final yield by approximately a factor of 5.

A more specific preparation and summary of structure analysis of $N^5$-methyl THHF and the intermediate compounds are set out below.

$N^5$-methyltetrahydrohomofolic acid is prepared by a general modus as noted above in the methods of Sakami and of Gupta and Huennekens, ante, for the preparation of the folate compounds. The present synthesis involves the condensation of formaldehyde with tetrahydrohomofolate to yield the $N^5$, $N^{11}$-methylenetetrahydrohomofolate followed by reductive cleavage of the latter with borohydride. As noted in the folate series, this cleavage is highly selective and little or no cleavage occurs on the $N^5$ side of the methylene bridge. The starting material, tetrahydrohomofolic acid, was prepared by catalytic hydrogenation of homofolic acid at a slight overpressure with platinum oxide. The catalyst was removed by filtration and formaldehyde added immediately. After heating to 55°C a solution of sodium borohydride was added and the mixture incubated at 55°C for 2 hours. For structure purposes, the resulting reaction mixture was chromatographed on a DEAE-cellulose column using an ammonium acetate gradient. $N^5$-methyltetrahydrohomofolate was identified as the main peak and isolated by precipitation with absolute ethanol as a white powder in 46% yield. The product was characterized by elemental analysis, paper and thin layer chromatography and absorption spectra at pH 1, 7 and 13.

The cyclic compound $N^5$, $N^{11}$-methylenetetrahydrohomofolate which is an intermediate in the preparation of $N^5$-methyltetrahydrohomofolate was prepared and isolated as follows. Homofolic acid was reduced to tetrahydrohomofolic acid as above by catalytic hydrogenation, formaldehyde added immediately, and the mixture incubated at 55°C for 30 minutes. The reaction mixture was then chromatographed on DEAE cellulose using a gradient of triethylammonium bicarbonate (TEAB) containing 1% formaldehyde and 0.5% mercaptoethanol. Again the product was precipitated with ethanol as a white powder. Characterization was by elemental analysis, absorption spectra at different pH's and paper and thin layer chromatography. Reduction with sodium borohydride gave the main product $N^5$-methyltetrahydrohomofolic acid.

$N^5N^{11}$-methenyltetrahydrohomofolic acid is produced by the reaction of THHF with formic acid to give several products depending on reaction conditions where the main product, isolated by DEAE cellulose chromatography, was shown to be $N^5$, $N^{11}$-methenyltetrahydrohomofolic acid as characterized by paper and thin layer chromatography and by absorption spectra.

The tetrahydrohomofolic acid derivatives of the present invention have been shown to have substantial anti-leukemia activity against L1210-FR8 tumor in mice and the advantage therapeutically is enhanced by the fact that these compounds show greater stability towards oxidation than the parent compound. The activity of the compound is believed at least in part to have the function as an inhibitor of thymidylate synthetase. Each of these compounds may be prepared as the free acid or preferably as an alkali metal disalt of the glutamate fraction, such as disodium salt.

The product compounds exist in the form of racemates due to the presence of an asymmetric carbon atom at the 6 position. Thus, the stereochemical designation is (d,1).

EXAMPLE I

Preparation of 5-Methyltetrahydrohomofolic Acid (Sodium Salt) NSC-139490

Platinum oxide, 3.0 g, was washed with four 20 ml portions of water and was hydrogenated in 130 ml of water at 4 cm overpressure, while stirring vigorously at room temperature. Reduction was complete in 2 hours and 50 minutes with absorption of 410 ml of hydrogen.

Homofolic acid (NSC-79249), 5.4 g, was suspended in 200 ml of water and 22 ml of 1 M sodium hydroxide was added dropwise (to pH 7.0) over a period of 1 hour while stirring with exclusion of light. The stirring was continued for an additional hour and thus obtained yellow solution was injected into the hydrogenation vessel. Hydrogenation at 4 cm over-pressure was complete in 4 hours and 50 minutes with absorption of 590 ml of hydrogen. The reaction mixture was filtered under argon through a glass sintered funnel and the filtrate was transferred into a 2 liter 3-neck flask which was flushed with argon.

Formaldehyde solution (37%), 2.9 ml, was added, the system was flushed with argon and the reaction mixture was heated to 55°C while stirring under argon with exclusion of light. 90 ml of a 1.0 M sodium borohydride solution was added rapidly and the reaction mixture was subsequently incubated at 55°C for 2 hours, at which time the evolution of hydrogen has practically stopped.

The reaction mixture was cooled to room temperature, 8 ml of mercaptoethanol was added and thus obtained a light yellow-colored solution was adjusted to pH 3.8 with glacial acetic acid on a pH meter. The resulting cloudy solution was refrigerated at 3°C overnight.

A beige-colored precipitate, containing the impurities, was collected on a Büchner Funnel and the pale straw-colored filtrate was stirred with 500 mg of Norit A for 20 minutes and was filtered. Evaporation at reduced pressure gave a viscous oil. The oily residue was thoroughly triturated with 900 ml of cold ethanol and thus obtained suspension of a white, solid material which was refrigerated for one hour and then stirred for one hour while cooling in ice. The white, fluffy precipitate was collected on a Büchner Funnel, washed repeatedly with cold ethanol, dried for 5 hours on high vacuo and was stored in vacuo.

The product was consistently in accord with the accepted criteria for purity.

| uv-spectra, | mμ; | λmin | λmax | λmin | λmax |
|---|---|---|---|---|---|
| | pH 1 | 245 | 266 | 285 | 291 |
| | pH 7 | 247 | 291.5 | — | — |
| | pH 13 | 246.5 | 287.5 | — | — |

Tlc; cellulose, solvent system; 0.1 M phosphate buffer; pH 7, 1% mercaptoethanol; Rf 0.80 quenching.

Analytical data: Calculated: C, 45.5; H, 5.25; N, 17.0; Na, 8.3. Found: C, 45.4; H, 4.8; N, 17.7; Na, 8.4.

EXAMPLE II

Preparation of 5,11-Methylenetetrahydrohomofolic Acid 3.2 g of $PtO_2$ was washed four times with water and hydrogenated with the absorption of 595 ml of $H_2$ in 3 hours 10 minutes. 5.5 g homofolic acid was hydrogenated with absorption of 600 ml of $H_2$ in 4 hours 10 minutes utilizing the reduced platinum catalyst. The product was filtered under argon and 1.6 of formaldehyde was added. The product was lyophillized and stored in a deep freeze.

The next day the product (in solution in water) was incubated for 6 hours at 55°C with an additional 16.5 ml of formaldehyde under argon. The reaction mixture was then cooled to room temperature and stirred for 20 minutes with 300 mg Norit A. 30 ml of acetic acid was added while stirring and the pH was adjusted to about 3.5. An off-white precipitate collected which was washed with alcohol, dried, and stored in vacuo. The product, 5,11-methylene THHF, sodium salt, had the following physical characteristics.

| uv-spectra, | mμ; | λmax | λmin | λsh |
|---|---|---|---|---|
| | pH 1 | 278 | 255 | 307 |
| | ph 7 | 303 | 259 | — |
| | pH 13 | 295 | 260 | — |

Tlc; cellulose, solvent system; 0.1 M phosphate; buffer pH 7, 1% mercaptoethanol; Rf 0.95 (quenching).

Analytical data: Calculated: C, 48.1; H, 4.58; N, 18.7. Found: C, 48.5; H, 5.9; N, 17.8.

EXAMPLE III

Preparation of 5,11-Methenyltetrahydrohomofolic Acid 2.0 g of THHF was dissolved in 200 ml of formic acid and heated under argon for 2 hours at 90°C, cooled to room temperature and evaporated at reduced pressure at 30°C. The residual oil was triturated in ethanol and refrigerated overnight.

The suspension was stirred in ice for 30 minutes and was filtered through a Büchner Funnel. The filter cake was washed repeatedly with cold alcohol and evacuated on a high vacuum for 2 hours, followed by drying overnight in vacuo.

| uv-spectra, | mμ; | λmin | λmax | λmin | λmax |
|---|---|---|---|---|---|
| | pH 1 | 266 | 289 | 298 | 324 |
| | pH 7 | 268 | 283 | 297 | 329 |
| | pH 13 | 241 | 255 | — | — |

Tlc; cellulose, solvent system; 0.1 M phosphate; buffer pH 7, 1% mercaptoethanol; Rf 0.60 (yellow fluorescence).

Analytical data: Calculated: C, 44.37; H, 4.54; N, 16.49; Na, 7.73. Found: C, 44.44; H, 5.02; N, 14.84; Na, 4.10.

In all examples element analysis, u.v. (ultraviolet), and tlc (thin layer chromatography) were performed.

EXAMPLE IV

Platinum oxide (1.0 gm) was hydrogenated in water (50 ml) at room temperature. The uptake of hydrogen was 110 ml.

Homofolic acid was dissolved in water (100 ml) with the addition of 1M sodium hydroxide solution to pH 7.0. Hydrogenation was carried out in 2½ hours with the uptake of 293 mls of hydrogen. The reaction was carried out in the dark.

The solution was filtered under argon and 37% formaldehyde (0.62 ml) added immediately. The mixture was warmed to 55°C and 1M sodium borohydride solution (43 ml) added. After incubation at 55°C for 2 hours the solution was cooled and mercaptoethanol (3.54 ml) and glacial acetic acid (2.85 ml) added. The pH was now 7.0.

The mixture was applied under anaerobic conditions to a column of DEAE cellulose (4 × 40 cm) and eluted with a gradient of ammonium acetate pH 7.0 (0.05M to 0.6M) containing 0.01M mercaptoethanol. Fractions were pooled on the basis of their uv absorbance.

The pH was adjusted to 3.8 by HAc and the mixture was cooled to 3°C overnight. Subsequently, the product was isolated by evaporation to an oil and precipitation in cold ethanol. The yield was 1.37 gms, 51°; uv spectrum, $\lambda_{max}$ 291, $\lambda_{max}$ 247.5; $\epsilon_{max}$ 24,000, paper chromatography 0.53 wk BF, 0.84 strong q; elemental analysis, found: C, 49.5; H, 6.6; N, 20.2; ash 0.00; calc: C, 49.5; H, 6.1; N, 19.25; ash 0.00.

Flow Sheet

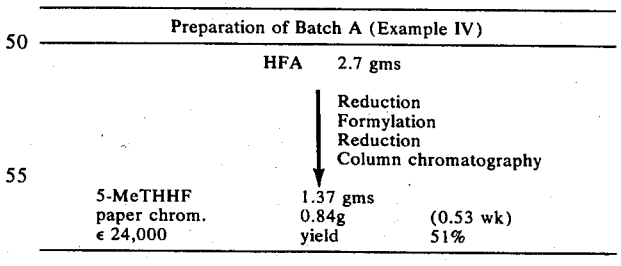

In Example IV the reduction and formylation above were carried out in the dark. HAc was utilized to adjust to a pH of 3.8 for separation of the product 5 Me-THHF and the impure product was refrigerated overnight at 3°C.

EXAMPLE V

The preparation was carried out exactly as described above in Example IV, using homofolic acid (4.5 gms).

The product was isolated by column chromatography in yield 3.64 gms, 78%. Paper chromatography showed one spot 0.78 q; uv absorbance at pH 7.0, $\lambda_{max}$ 291.5, $\lambda_{min}$ 247; $\epsilon_{max}$ 21,400; $A_{max}/A_{min}$ 3.9.

| Preparation of Batch B (Example V) | |
|---|---|
| HFA | 4.5gms |
| | Reduction |
| | Formylation |
| | Reduction |
| | Column chromatography |
| 5-METHHF | 3.64 gms |
| paper chrom. | 0.78q |
| $\epsilon$ 21,400 | yield 78% |

In Example V the reduction and formylation above were carried out in the dark. HAc was utilized to adjust to a pH of 3.8 for separation of the product 5 Me-THHF and the impure product was refrigerated overnight at 3°C.

EXAMPLE VI

Using the process of Example I, one additional batch of product was prepared utilizing HFA as a starting material with the following schematic results.

Flow Sheet

| I. Preparation of Batch C (Example VI) | |
|---|---|
| HFA | 5.4 gms |
| | Reduction |
| | Formylation |
| | Reduction |
| | Precipitation |
| 5-MeTHHF | 4.05 gms, 75% |
| Paper chrom. 0.79q (0.345, 0.63 wk) | |

| II. Preparation of Batch D (Example I) | |
|---|---|
| HFA | 5.4 gms |
| | Reduction |
| | Formylation |
| | Reduction |
| | Precipitation |
| 5-MeTHHF, 5.0 gms, 92% | |
| paper chrom. satisfactory | |

In Example VI the reduction and formylation above were carried out in the dark. HAc was utilized to adjust to a pH of 3.8 for separation of the product 5 Me-THHF and the impure product was refrigerated overnight at 3°C.

EXAMPLE VII

Preparation of 5-Me THHF by Comparative Experiment Using THHF as a Starting Material A. Tetrahydrohomofolic acid (2.0 gm) was dissolved in water (20 ml) at pH 7.0, which had been previously flushed with nitrogen for 1 hour. The system was flushed thoroughly with nitrogen. Formaldehyde (0.45 ml, 37%) was added and the mixture heated to 55°C. Sodium borohydride (31.7 ml 1M solution) was added and the solution incubated at 55°C for 2 hours. Mercaptoethanol (2.64 ml) and glacial acetic acid (1.85 ml) were added and the mixture diluted to 500 ml. The solution was frozen and stored overnight.

The next day the solution was applied to a column of DEAE cellulose (4 × 27 cm). The column was developed with a gradient of ammonium acetate pH 7.0 (0.01 M to 0.6 M) containing 0.05% mercaptoethanol. Four peaks were obtained. The main peak of 5-Me THHF was identified by its uv spectrum ($\lambda_{max}$ 290 nm) and pooled, evaporated to an oil and lyophilised. The yield was 1.95 gms. Paper chromatography on Whatman No. 1 paper in a solvent system of 0.1M phosphate pH 7.0, 0.5% mercaptoethanol showed four spots 0.49 BF*, 0.56 BF, 0.69 wk, BF, 0.83 VQ**.

\* BF = blue fluorescent
\*\* VQ = violet quenching

5 Me-THHF (1.95 gms) was dissolved in deaerated water (100 ml) containing 0.01 M mercaptoethanol and chromatographed on a column of DEAE cellulose under nitrogen. A gradient of ammonium acetate pH 7.0 (0.0 to 0.4 M) containing 0.01 M mercaptoethanol was used. One broad peak was eluted. Pooling was carried out on the basis of uv absorbance ($\lambda_{max}$ 290 nm). After evaporation and removal of salts, the product was combined with B, below.

B. The reaction was carried out as described previously using tetrahydrohomoforlate (4.0 gms), water 40 ml), formladehyde (0.90 ml) and sodium borohydride (63.4 ml 1M solution). The total volumn of the mixture was 200 ml and incubation was at 55°C for 2 hours.

After the reaction mercaptoethanol (5.28 ml) and glacial acetic acid (3.70 ml) were added and the mixture chromatographed immediately on a column of DEAE cellulose (4 × 30 cm). The column was washed and then eluted with a gradient of ammonium acetate pH 7.0 (0.01 M to 0.6 M) containing 0.5% mercaptoethanol. Three peaks were obtained. The main peak was identified as 5-Me THHF by its uv spectrum and pooled, evaporated and lyophilised. The yield was 1.93 gms. Paper chromatography showed four spots of equal intensity 0.16 BF, 0.38 BF, 0.46 BF, 0.67 VQ.

The product was dissolved in water (75 ml), containing 0.01 M mercaptoethanol under nitrogen and rechromatographed. The column chromatography was carried out at 4°C, all solutions were precooled and rigorous precautions taken to insure anerobic conditions. All solutions were degassed and the column and tubes were maintained in a nitrogen atmosphere using a dry bag. Light were excluded by wrapping the column, all connecting tubing, and fraction collector in aluminum foil.

The gradient was ammonium acetate pH 7.0 (0.0 to 0.6 M) containing 0.01 M mercaptoethanol. One peak was obtained. A cut was made of fractions with $\lambda_{max}$ 290 nm. The product was collected by evaporation and lyophilization. Paper chromatography showed impurities and so the material was combined with A above.

The combined material was chromatographed on DEAE cellulose using a gradient of ammonium acetate containing mercaptoethanol as described above. Fractions were pooled on the basis of their $\lambda_{max}$ in the uv spectrum. Paper chromatograms, also developed under nitrogen, showed two spots 0.48 BF and 0.78 Q.

A fourth column was run. The material isolated showed only a trace of the spot at 0.48 on paper chromatography. The product was isolated by evaporation to remove water and salts followed by precipitation with ethanol containing HCl. The precipitate was collected under nitrogen, washed with cold ethanol and dired in vacuo, yield mg (6.67%), uv spectrum (ph 7.0) $\lambda_{max}$ 291, $\lambda_{min}$ 246.5 nm; $\epsilon_{max}$ 22,600; $A_{max}/A_{min}$ 3.7; m.p. 215°–219°C; elemental analysis, found: C, 45.5; H, 6.0; N, 17.8; ash, 0.0; Cl, 0.0; calc: C, 46.6; H, 6.4; N, 17.9; ash, 0.00.

Flow Sheet

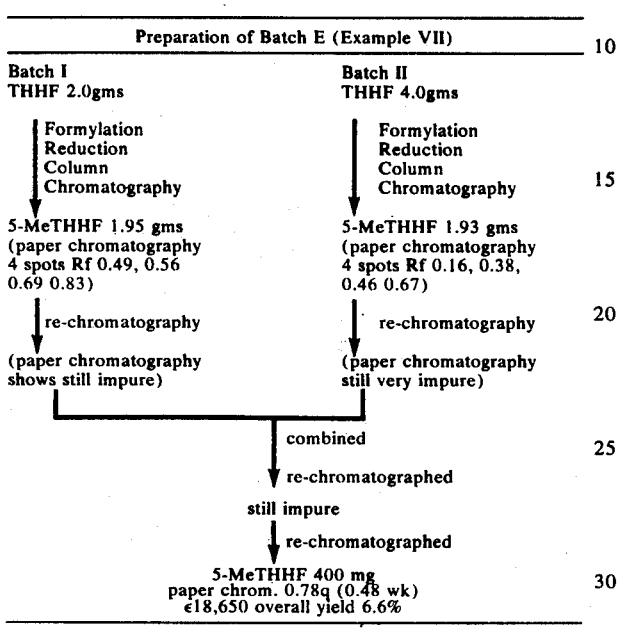

In Example VII the formylation and borohydride reduction above were carried out in the dark.

What is claimed is:

1. In the preparation of $N^5$-methyltetrahydrohomofolic acid from homofolic acid, the steps consisting of reducing homofolic acid to tetrahydrohomofolic acid in the dark with a slight overpressure of hydrogen in the presence of reduced platinum oxide, immediately reacting tetrahydrohomofolic acid with formaldehyde to product the intermediate 5,11-methylenetetrahydrohomofolic acid and reducing without isolation the formed 5,11-methylene intermediate with sodium borohydride to give the desired 5-methyltetrahydrohomofolic acid (5-MeTHHF) and removing by precipitation at a pH of about 3.8 with acetic acid the side products, refrigerating the product filtrate containing 5-MeTHHF overnight and separating and recovering 5-MeTHHF.

* * * * *

UNITED STATES PATENT OFFICE
CERTIFICATE OF CORRECTION

PATENT NO. : 3,983,118
DATED : September 28, 1976
INVENTOR(S) : Roger L. Knott, Alison Taunton-Rigby, and John A. R. Mead It is certified that error appears in the above-identified patent and that said Letters Patent are hereby corrected as shown below:

The full name of the second inventor is not shown on the face of the patent. It should be Alison Taunton-Rigby.

Signed and Sealed this

First Day of February 1977

[SEAL]

Attest:

RUTH C. MASON
*Attesting Officer*

C. MARSHALL DANN
*Commissioner of Patents and Trademarks*